United States Patent
Barbieri et al.

(10) Patent No.: US 10,127,271 B2
(45) Date of Patent: Nov. 13, 2018

(54) GENERATING A QUERY

(71) Applicant: KONINKLIJKE PHILIPS N.V., Eindhoven (NL)

(72) Inventors: Mauro Barbieri, Eindhoven (NL); Johannes Henricus Maria Korst, Eindhoven (NL); Pavankumar Murli Dadlani Mahtani, Eindhoven (NL); Zarko Aleksovski, Eindhoven (NL); Marc Andre Peters, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 752 days.

(21) Appl. No.: 14/020,092

(22) Filed: Sep. 6, 2013

(65) Prior Publication Data

US 2014/0067847 A1  Mar. 6, 2014

Related U.S. Application Data

(60) Provisional application No. 61/697,331, filed on Sep. 6, 2012.

(51) Int. Cl.
*G06F 17/30* (2006.01)
*G06F 19/00* (2018.01)

(52) U.S. Cl.
CPC .. *G06F 17/30389* (2013.01); *G06F 17/30637* (2013.01); *G06F 17/30672* (2013.01); *G06F 19/324* (2013.01)

(58) Field of Classification Search
None
See application file for complete search history.

(56) References Cited

U.S. PATENT DOCUMENTS

| 5,619,709 | A  | * | 4/1997  | Caid ................ G06F 17/30265 704/9 |
| 6,675,159 | B1 | * | 1/2004  | Lin et al. |
| 9,104,750 | B1 | * | 8/2015  | Dhamdhere ........ G06F 17/3064 |
| 2002/0062229 | A1 | * | 5/2002  | Alban et al. ...................... 705/3 |
| 2003/0028512 | A1 | * | 2/2003  | Stensmo ........... G06F 17/30687 |
| 2007/0043742 | A1 | * | 2/2007  | Arguello ........... G06F 17/30734 |
| 2007/0294289 | A1 | * | 12/2007 | Farrell .............. G06F 17/30958 |

(Continued)

OTHER PUBLICATIONS

Tang, P.C. et al, "Informing Patients: A Guide for Providing Patient Health Information." Journal of the American Medical Informatics Association, vol. 5, No. 6, Nov./Dec. 1998 pp. 563-571.

(Continued)

*Primary Examiner* — Tyler Torgrimson

(57) ABSTRACT

A system for generating a query includes a term unit (1) for extracting a term from at least one input document (51), to obtain an extracted term. A category unit (2) is arranged for associating the extracted term with a category that is semantically related with the extracted term. A query unit (3) is arranged for generating a query in dependence on the extracted term and the category. The query unit (3) includes an additional term unit (4) for generating at least one additional search term based on the category, and the query unit (3) is arranged for including the additional search term in the query. A submit unit (5) is arranged for submitting the query to at least one search engine (50), to obtain a plurality of found documents.

17 Claims, 1 Drawing Sheet

(56) References Cited

U.S. PATENT DOCUMENTS

| | | | |
|---|---|---|---|
| 2008/0201280 A1* | 8/2008 | Martin | G06N 99/005 |
| | | | 706/12 |
| 2009/0300046 A1* | 12/2009 | Abouyounes | 707/102 |
| 2010/0312798 A1* | 12/2010 | Dutta et al. | 707/780 |
| 2011/0047149 A1* | 2/2011 | Vaananen | 707/723 |
| 2011/0225002 A1 | 9/2011 | Fackler et al. | |
| 2012/0150498 A1* | 6/2012 | Shastri | G06Q 50/22 |
| | | | 703/2 |

OTHER PUBLICATIONS

Zhu, S. et al. "Enhancing MEDLINE document clustering by incorporation MeSH semantic similarity." Bioinformatics. vol. 25, No. 15, 2009, pp. 1944-1951.

Cimino, J.J. "Auditing the United Medical Language System with Semantic Methods." Journal of the American Medical Informatics Association, vol. 5, No. 1, Jan./Feb. 1998, pp. 41-51.

Soderland, S. et al. "Machine Learning of Text Analysis Rules for Clinical Records." University of Massachusetts, Amherst, MA.

Smith, M. et al. "Readability and Understandability: Different Measures of the Textual Complexity of Accounting Narrative." Accounting, Auditing and Accountability Journal, vol. 5, Issue 4, 1992, Abstract Only.

* cited by examiner

GENERATING A QUERY

FIELD OF THE INVENTION

The invention relates to generating a query.

BACKGROUND OF THE INVENTION

Patient-centric solutions and patient empowerment are current trends in healthcare. It has been found that it may be beneficial to involve patients and their families more in their healthcare. Patient satisfaction, experience and empowerment are important factors for medical practice.

During a care cycle (e.g. cardiology or oncology), patients are typically overwhelmed with the amount of information accessible to them. In the case of chronic diseases such as cancer, patients tend to receive and seek a lot of information. Many times, once diagnosed, patients do not know where to start looking for the right information, nor do they understand what information they should look for, i.e. information that is relevant and necessary for them. This is partly due to them still having to cope emotionally and psychologically with their condition, and partly due to lack of guidance.

It is known that regardless of the (comprehensive) information that patients receive from their care provider, even if it is considered to be complete information/educational material, patients will still seek for more sources, either online or via their personal network. For example, patients can use an Internet search engine, such as Google, to search for information relating to their disease, by submitting a query into the search engine and reviewing the search results. For example, the user can submit a query with the name of their disease.

"Informing Patients: A Guide for Providing Patient Health Information", by Paul C. Tang et al., in Journal of the American Medical Informatics Association, Volume 5, Number 6, November/December 1998, discusses patients' need for information surrounding ambulatory-care visits. The document discloses providing printed summary information to patients at the end of a clinic visit to improve their understanding of their care.

SUMMARY OF THE INVENTION

It would be advantageous to have an improved system for generating a query. To better address this concern, a first aspect of the invention provides a system comprising a term unit for extracting a term from at least one input document, to obtain an extracted term;

a category unit for associating the extracted term with a category that is semantically related with the extracted term;

a query unit for generating a query in dependence on the extracted term and the category.

Since the query is generated based on the term extracted from the input document and the category of this term, the query unit is capable of adapting the query to this category. This way, information that is particularly relevant for a user, in view of the input document, can be retrieved by the query. For example, the system may be used to support clinicians and patients to generate a personalized educational 'prescription' that is tailored to the needs and situation of a particular patient. The term unit helps to find an appropriate term from the input document. This way, the user does not have to think of an appropriate term. The query may thus be generated automatically from the input document. For example, at least one document from the patient's health record may be used as the at least one input document.

The query unit may comprise an additional term unit for generating at least one additional search term based on the category. The query unit may be arranged for including the additional search term in the query. This is an efficient way to adapt the query to the category. For example, if the extracted term is 'acetaminophen' and the category of the extracted term is 'medicine', a query comprising the search term 'side effect of' may be generated, resulting in a query 'side effect of acetaminophen'.

The system may comprise a submit unit for submitting the query to at least one search engine, to obtain a plurality of found documents. This way the user may be presented with the search result, without having to bother about the query or search engine. The system may be arranged for submitting the query to more than one search engine, to obtain more found documents.

The system may comprise a comparator for comparing at least one found document of the plurality of found documents with said at least one input document, to determine a value representing a relevance of the found document in respect of said at least one input document. This way, a ranking of the found documents may be performed. Such a ranking can be used to sort or select the found documents. This makes the result more useful. For example, the documents found for a query may be relevant for the query but not necessarily for the context (input document) from which the query was derived. By determining a relevance value for the found document based on the input document, the found documents that are relevant for the context, as described in the input document, are detected by means of a higher relevance value. Then, for example only the most relevant documents are presented to the user.

The system may comprise a result filter for selecting at least one document of the plurality of found documents, based on a clinical pathway of a patient associated with said at least one input document. The clinical pathway of the patient may comprise additional information that can be used by the system to filter the documents.

The system may comprise a complexity unit for ranking the plurality of found documents based on a complexity of each document. This makes the result more useful, because the complexity of the documents offered to the user may be adapted to the complexity that the user can handle.

The system may comprise a case unit for determining first case information associated with said at least one input document, wherein the first case information relates to a first case. The system may further comprise a similarity unit for determining second case information, wherein the second case information relates to a second case, wherein the second case is similar to the first case based on predetermined similarity criteria. The query unit may be arranged for generating the query further based on the second case information. This allows performing a query that is not only based on the input document itself, but also on related documents. This way, for example, queries associated with the second case information may be re-used, possibly after adaptation, to generate the query for the at least one input document.

The at least one input document may comprise a medical report or be part of an electronic medical record of a patient. Likewise, the case information may comprise at least part of the electronic medical record of the patient. These features may be useful to generate a query to find educational material for a patient in respect of the condition of the patient or concerns of the patient, based on the information in the medical report or the medical record of the patient.

The query generator may be arranged for generating the query to search educational material to educate a patient regarding the patient's medical condition. This is an efficient way to provide suitable educational material.

In another aspect, the invention provides a workstation comprising the system set forth.

In another aspect, the invention provides a method of generating a query, comprising extracting a term from at least one document in dependence on an ontology, to obtain an extracted term;

associating the extracted term with a category that is semantically related with the extracted term, based on the ontology; and generating a query in dependence on the extracted term and the category.

In another aspect, the invention provides a computer program product comprising instructions for causing a processing unit to perform the method set forth.

It will be appreciated by those skilled in the art that two or more of the above-mentioned embodiments, implementations, and/or aspects of the invention may be combined in any way deemed useful.

Modifications and variations of the workstation, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1:
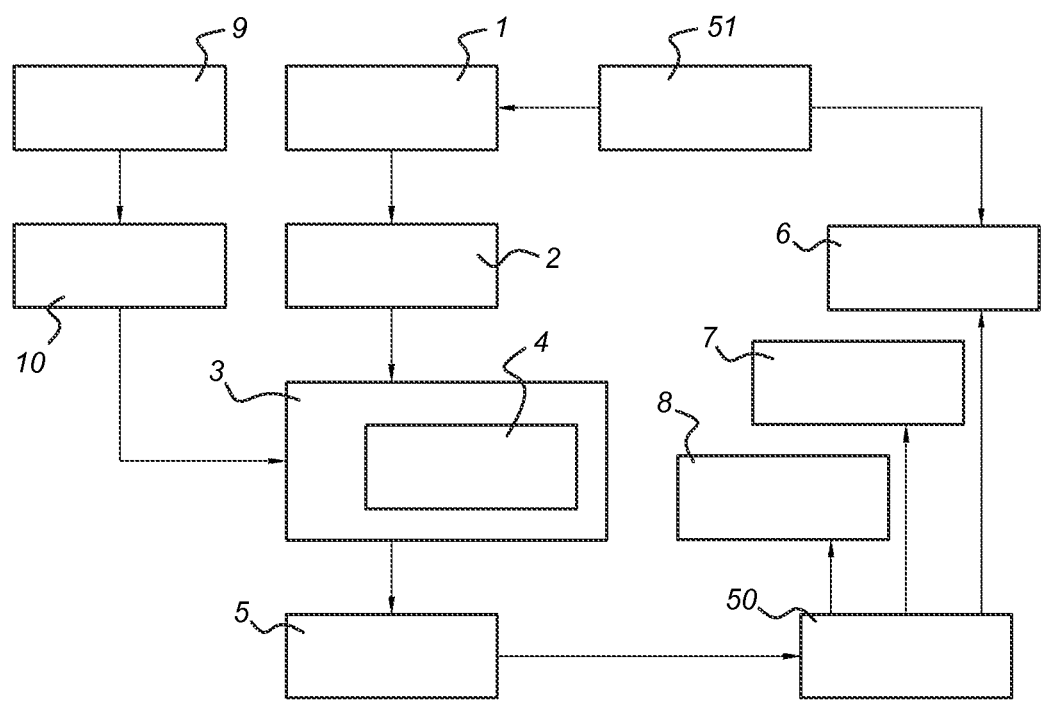
FIG. 1 is a block diagram illustrating aspects of a query system.

FIG. 1 shows a block diagram of a query system. The system may be used to generate a query. Optionally, the system may further be arranged for submitting the query to a search engine, and providing a post-processing of the found documents. The system may be implemented by means of dedicated electronic circuitry. Alternatively, the system may be implemented by means of a suitably programmed computer system. The computer system may be a server system. The query system described herein may be, for example, a module of a healthcare information system. Alternatively, the system may be implemented on a workstation.

The system may comprise a control unit (not shown) that activates the query generation by appropriately controlling the units described hereinafter. The control unit may be operatively coupled to a user interface or to a larger system, such as a healthcare information system. For example, the system may be triggered when a new document arrives in the system, or when a major diagnosis has been made in respect of a patient.

The system may comprise a term unit 1 for extracting a term from at least one input document 51, to obtain an extracted term. This extraction may be performed, for example, by comparing the terms appearing in the document against a predetermined collection of terms that are eligible for searching. Such a collection of terms may be associated with an ontology, so that the term extraction can use the structure provided in the ontology to extract similar terms. Optionally, a plurality of search terms are extracted.

The system may comprise a category unit 2 for associating the extracted term with a category that is semantically related with the extracted term. To determine the category, the ontology may be used for example. Alternatively, a list of categories with associated terms may be provided to the system a priori.

The system may comprise a query unit 3 for generating a query in dependence on the extracted term and the category. This query unit may be arranged for including the extracted term into the query. Moreover, additional components of the query may be included, based on the category. For example, a kind of documents or a date range of documents searched may be made dependent on the category.

The generated query or queries may be output to a user, so that the user can select which queries to search. Moreover, the user may be enabled to edit the queries.

The query unit 3 may comprise an additional term unit 4 for generating at least one additional search term based on the category. The query unit 3 may be arranged for including the additional search term into the query. Moreover, a plurality of queries may be generated for a category. For example, for a category 'medicine', a first query including the term 'effectiveness' and a second query including the term 'side effects' may be generated.

The system may comprise a submit unit 5 for submitting the query to at least one search engine 50, to obtain a plurality of found documents. For example, the search engine 50 may be a database search engine, searching a set of locally hosted documents. Alternatively, the search engine may be an Internet search engine. Other kinds of search engines may also be used.

The system may comprise a comparator 6 for comparing at least one found document of the plurality of found documents with said at least one input document. This way, the comparator 6 may determine a value representing a relevance of the found document in respect of said at least one input document. This will be described in more detail elsewhere in this description.

The system may comprise a result filter 7 for selecting at least one document of the plurality of found documents, based on a clinical pathway of a patient associated with said at least one input document. For example, based on the clinical pathway, some documents are more relevant for the patient than other documents, based on predetermined selection criteria. The result filter 7 applies these selection criteria to the found documents, in order to filter out the most relevant documents.

The system may comprise a complexity unit 8 for determining a complexity of at least one of the found documents. Determining the complexity is explained in more detail elsewhere in this description. The complexity may be adapted to the level of skills of the patient.

The system may comprise a case unit 9 arranged for determining first case information associated with the input document. This first case information relates to a first case, such as a patient case. For example, the case information is at least part of a medical record of the patient. The system may comprise a similarity unit 10 for determining second case information, wherein the second case information relates to a second case, wherein the second case is similar to the first case based on the first case information, the second case information, and predetermined similarity criteria. A similarity assessment mechanism, as described elsewhere in this description, may be employed. For example, the second case information is the medical record of another patient. Alternatively, the first and/or second case information may be user profiles in a medically-oriented social media website, for example.

The query unit 3 may be arranged for generating the query further based on the second case information. For example, the second case information may be associated with one or more queries or search terms. These latter queries and/or search terms may be associated with a level of usefulness that the second case's patient has attached thereto. Those ingredients may be used to generate the query.

The at least one input document 51 may comprise a medical report. The input document 51 may also be part of an electronic medical record of a patient. For example, the term unit 1 is operatively coupled to a healthcare information system to retrieve the document therefrom.

The query generator 3 may be arranged for generating the query to search educational material to educate a patient regarding the patient's medical condition.

Figure 2:
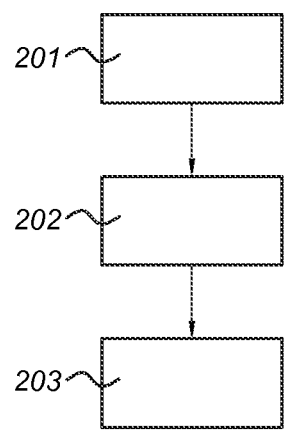
FIG. 2 is a flowchart illustrating aspects of a query method.

FIG. 2 illustrates a method of query generation. In step 201, a term is extracted from at least one document in dependence on an ontology, to obtain an extracted term. In step 202, the extracted term is associated with a category that is semantically related with the extracted term, based on the ontology. In step 203, a query is generated in dependence on the extracted term and the category. It will be understood by the person skilled in the art, that the method may be extended and/or modified based on the description of the functionality of the system. The method, as well as the system, is suited for being implemented at least partly by means of software in a computer program product.

A tool is described herein that may be used to support clinicians and patients to generate a personalized educational program and guidance for a patient, such that the patient is educated with the right educational material, at the right time and/or in the right way. By examining the patient's documents, including one or more of the following: patient's profile and Electronic Health Record (EHR), diagnosis report, pathology, co-morbidity reports and referral letters from other practitioners, the system may generate an 'educational prescription' for the patients comprising educational sources (websites, articles, etc.) provided in a meaningful, filtered, and orderly manner to the patient. A medical ontology may be used to textually analyse the patient's document to extract relevant medical terms, alternative synonymous, easier or broader terms. More specifically, given that the patient is usually not familiar with the Latin medical terms, Latin terms may be translated into the equivalent terms (if present) in a language of the patient's choice.

These terms may be used to generate a set of queries that are sent to possibly different content providers (e.g. PubMed, WebMD, Google, YouTube, etc.). Heuristics may be used to compose the queries. The queries typically contain one or more of the identified medical terms and additionally may contain phrases that improve the queries. These phrases are specific for the category of the medical term used. The system may issue these queries directly to the content providers and re-ranks and filters the returned results for the patient, taking into account the patient's set of documents (i.e. EHR and other information sources). In this way, the re-ranked and filtered results may be personalized to the given patient in two steps. In the first step, the patient's EHR is used to formulate appropriate queries, and in a second step, the returned results are filtered and re-ranked on the basis of the patient's EHR. Additionally, the returned results can also be filtered and re-ranked on the basis of their perceived complexity and by the used languages.

The queries could also be generated, not only by analyzing the situation of the user (i.e. diagnosis, pathology, etc.) but by also searching a patient community database. The system searches through the database and looks for patients with the same profile and clinical information, and provides the patient with popular ranked queries that other patients have used to search for information.

The system can further tailor the educational delivery by using the patient's pathway (i.e. using the chosen clinical pathway by the patient's physician based on standard operating procedures or clinical guidelines), and present only the relevant information and educational material depending on where the patient is in the treatment/patient pathway.

It will be clear that instead of directly issuing the given queries to the different content providers, the queries can also be shown to the patient who then can select the queries that he or she actually wants to be used.

In a first step, the patient's EHR and possibly other relevant sources (pathology reports, diagnosis, GP letters, imaging analysis, etc.) may be analyzed to identify relevant medical terms. For this, a medical ontology may be used. This ontology provides additional information for a given identified medical term, such as synonymous terms and broader terms. In addition, the category of the term is identified. Examples of categories are 'body structure', 'chemical substance' and 'clinical finding'. In addition, some text processing and semantic reasoning may be used to identify e.g. negations, to discriminate between sentences that state the presence of a disease and sentences that state the absence of it.

In a second step, the identified medical terms may be used to generate one or more specific queries that can be sent to one or more content providers (e.g. PubMed, WebMD, Google, YouTube, etc.) and/or local databases. To generate these queries, the identified medical terms may be combined with other terms that are specific for the category to which the medical term belongs. For example, if the identified medical term is a chemical substance, then it may be combined with phrases 'side effects of . . . ', 'dosage of . . . ', 'price of . . . ' or 'alternatives for . . . '. As another example, if the identified medical term is a clinical finding, then it may be combined with 'treatment', 'survival rate', etc. In addition to using the medical terms identified in the patient's EHR, one can also try to use the terms that are synonyms of the given terms. More specifically, given that the patient is usually not familiar with the Latin medical terms, these can be translated into the equivalent terms (if present) in a language of the patient's choice.

In a third step, these queries may be sent to the selected one or more information repositories, for example by means of a search API (application programming interface), that may allow a full-text search. The queries can be ranked from more-specific to less-specific. In this way, the system can first try to send the more specific queries. Then, in case the information repositories do not return enough results, the system could additionally send less-specific queries. By sending multiple queries to potentially multiple repositories, the system may collect a relatively large set of results. These results may not all be relevant to the patient at hand. To determine which results are actually being selected for presentation to the patient, the results can be compared to the patient's EHR and other documents. Those results that have a high overlap of the specific medical terms are probably most relevant. Additionally, the results can be compared with the patient's EHR on textual relatedness, not specifically focussing on the medical terms. For this, the documents can be characterized by the words that occur in them, using a so-called bag-of-words approach. A document can then be represented as a vector in a multi-dimensional space, where each dimension corresponds to a word in a given corpus or dictionary, possibly weighing the different words using the well-known term frequency-inverse document frequency (tf-idf) approach. Note that a result may also comprise audio or video items. The accompanying metadata, describing its content, can then be used to form a textual description. In addition, the patient's EHR can also be represented as a vector in the same multi-dimensional space. The relatedness between a result and the patient's EHR can be expressed as the angle between the corresponding vectors, i.e. by using the so-called cosine similarity. This similarity can be used to rank the results from more relevant to less relevant.

In a fourth step, the results can be further filtered or re-ranked by taking into account the textual complexity that the patient prefers. The textual complexity is determined, amongst others, by the language that is used in the document. For example, a native French or Dutch person of older age may not be able to read English texts. Additionally, the complexity of a given text could be further analysed by looking at specific parameters, such as the average number of words per sentence, the average number of characters per word, and the use of more or less specialized medical terms. The patient could express explicitly his preferences on textual complexity by (1) indicating which languages are permitted and (2) indicating whether he or she wants to restrict the results to introductory, medium or advanced. The desired textual difficulty could also be extracted from other sources. In addition, by tracking the past reading history, and measuring the complexity of read documents, the system may determine what is the textual complexity that the patient prefers.

After this filtering and re-ranking step, the results may be presented to the patient as a single list or as multiple lists. The results can be grouped on the basis of the content provider that produced the results or alternatively the results can be grouped based on the grouping of related queries, assuming that results of related queries are also related. Additionally, precedence relations between documents may be identified, indicating that first document A should be read before reading document B. In that case, document B may not be offered to the patient before the patient has read document A.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for generating a query to search educational material to educate a first patient regarding the first patient's medical condition, the system comprising:
   a term unit executed on one or more processors and configured to extract a term indicative of a medical condition or a medicine from at least one of a medical report or a part of an electronic medical record of the first patient to obtain an extracted term;
   a category unit executed on the one or more processors and configured to associate the extracted term with one of a list of categories that is semantically related with the extracted term, the list of categories including at least medical conditions and medicines;
   a similarity unit executed on the one or more processors and configured to determine second patient case information, wherein the second patient case information is associated with an electronic medical record of a second patient, wherein similarity is based on at least one of the medical report or the electronic medical record of the first patient, the second patient case information, and predetermined similarity criteria, wherein the second patient case information is associated with second case queries, and the second case queries are associated with levels of usefulness attached to each second query by the second case patient;

a query unit executed on the one or more processors and configured to generate a first query in dependence on the extracted term, the category, and the second patient case information and the associated second case queries with the attached levels of usefulness;

a submit unit executed on the one or more processors and configured to submit the first query to at least one search engine to obtain a plurality of found documents; and a comparator executed on the one or more processors and configured to compare at least one found document of the plurality of found documents with at least one of the medical report or the patient electronic medical record of the first patient to determine a value representing a relevance of the found document in respect of at least one of the medical report or the patient electronic medical record of the first patient.

2. The system according to claim 1, wherein the query unit comprises an additional term unit configured to generate at least one additional search term based on the category, and wherein the query unit is further configured to include the additional search term in the query.

3. The system according to claim 2, wherein the category includes medicines and the at least one additional search term is indicative of one of effectiveness and side effects.

4. A workstation comprising the system according to claim 1.

5. The system according to claim 1, further including:
a result filter configured to select at least one document of the plurality of found documents, based on a clinical pathway of the patient associated with said at least one of the medical report and the patient electronic medical record; and
a complexity unit configured to determine a complexity of at least one of the found documents.

6. The system according to claim 1, wherein the comparator is configured to rank the found documents including:
representing the medical report or part of the electronic medical record of the patient as a vector in a multi-dimensional space, each dimension of the multi-dimensional space corresponding to a word;
representing each of the found documents as a vector in the multi-dimensional space;
determining angles between the vector representing the medical record or part of the electronic medical record and the vectors representing the found documents;
ranking each found document based on a closeness of angle between the vector of the found document and the vector of the medical report or part of the medical record of the patient.

7. The system according to claim 6, further including a display device, the display device being configured to present the found documents based on the ranking.

8. The system according to claim 6, further including a filter configured to filter the found documents to permit only documents in one or more preselected languages and below a preselected level of linguistic complexity.

9. A system for generating a query to search educational material to educate a patient regarding the patient's medical condition, the system comprising:
one or more computers programmed to:
extract a term regarding the patient's medical condition or a medicine from an electronic medical record in an electronic medical records database to obtain an extracted term, wherein the electronic medical record includes at least one of a medical report or a medical record;
associate the extracted term with one of a list of medical categories that is semantically related with the extracted term, the list including medical conditions and medicines, the categories being indicative of one or more of body structure, chemical substance, and clinical finding;
generate an additional term that is indicative of one or more of side effects, dosage, price, alternatives, and survival rates;
generate a query in dependence on the extracted term, the additional term, and at least one category in the list of medical categories;
submit the query to at least one search engine to obtain a plurality of found documents;
compare at least one found document of the plurality of found documents with at least one of the medical report or the patient's medical record to determine a relevance of the found document to at least one of the medical report or the patient's medical record;
rank the documents by representing each document as a vector in multi-dimensional space, where each dimension corresponds to a word in a given dictionary;
represent the patient's electronic medical record as a vector in the multi-dimensional space;
determine angles between the vector representing the medical record or part of the electronic medical record and the vectors representing the found documents;
compare the angles between the document and electronic medical record vectors to determine similarity;
determine textual difficulty of each document; and
present documents to the patient based on the determined relevance, the determined similarity, and the determined textual difficulty.

10. The system according to claim 9, wherein the one or more computers are further configured to:
compare a portion of the patient's electronic medical record with electronic medical records of other patients;
determine a similarity of corresponding portions of the other patient's electronic medical records to the portion of the patient's electronic medical record; and
generate the query further based on information from a similar patient record of another patient.

11. The system according to claim 9, wherein the one or more computers are further configured to:
review electronic medical records for other patients to determine patients with a similar medical condition; and
wherein generating the query includes incorporating search terms which were useful in a prior query for a patient with the similar medical condition.

12. The system according to claim 9, wherein the patient's electronic medical record includes at least one of a diagnosis report, pathology, co-morbidity report, and practitioner referral letters.

13. The system according to claim 9, wherein the one or more computers are further configured to:
determine a relevance of each found document to where the patient is in a patient pathway based on clinical guidelines.

14. The system according to claim 9, wherein the one or more computers are further programmed to:
select at least one document of the plurality of found documents, based on a clinical pathway of the patient associated with said at least one of the medical report and the patient electronic medical record.

15. The system according to claim 9, wherein the extracted term is selected based on an ontology and the extracted term is associated with the one of the list of categories based on the ontology.

16. A system for generating a query to search educational material to educate a patient regarding the patient's medical condition, the system comprising:
one or more computers programmed to:
extract a term regarding the patient's medical condition or a medicine from an electronic medical record in an electronic medical records database to obtain an extracted term, wherein the electronic medical record includes at least one of a medical report or a medical record;
associate the extracted term with one of a list of medical categories that is semantically related with the extracted term, the list including medical conditions and medicines, the categories being indicative of one or more of body structure, chemical substance, and clinical finding;
generate an additional term that is indicative of one or more of side effects, dosage, price, alternatives, and survival rates;
generate a query in dependence on the extracted term, the additional term, and at least one category in the list of medical categories;
submit the query to at least one search engine to obtain a plurality of found documents;
compare at least one found document of the plurality of found documents with at least one of the medical report or the patient's medical record to determine a relevance of the found document to at least one of the medical report or the patient's medical record;
rank the documents by representing each document as a vector in multi-dimensional space, where each dimension corresponds to a word in a given dictionary;
represent the patient's electronic medical record as a vector in the multi-dimensional space;
determine angles between the vector representing the medical record or part of the electronic medical record and the vectors representing the found documents;
compare the angles between the document and electronic medical record vectors to determine similarity;
determine textual difficulty of each document; and
present documents to the patient based on the determined relevance, the determined similarity, and the determined textual difficulty;
an electronic medical records database configured to store the medical records of the patient; and
a display apparatus configured to present the documents to the medical report or the patient's medical record to the patient.

17. The system according to claim 16, wherein the presented documents are more relevant than a selected relevance threshold, more similar than a selected similarity threshold, and textually simpler than a selected textual difficulty threshold.

* * * * *